United States Patent [19]

Lenhardt

[11] 4,237,422
[45] Dec. 2, 1980

[54] CHROMATOGRAPH SIGNAL GENERATOR

[75] Inventor: Wilfried K. Lenhardt, Richardson, Tex.

[73] Assignee: Mobil Oil Corporation, New York, N.Y.

[21] Appl. No.: 938,275

[22] Filed: Aug. 31, 1978

[51] Int. Cl.³ .......................... H03K 3/01; H03K 3/04
[52] U.S. Cl. .......................................... 328/61; 73/23.1;
 210/31 C; 307/228; 328/63; 328/104; 328/156
[58] Field of Search .................. 328/61, 63, 103, 104,
 328/156, 157, 158, 159; 307/228; 73/23.1;
 210/31 C, 31 R

[56] References Cited
U.S. PATENT DOCUMENTS

| 3,573,637 | 4/1971 | Stebbins | 307/228 |
| 3,803,500 | 4/1974 | Taudt et al. | 307/228 |
| 3,879,724 | 4/1975 | McDonald | 328/158 |
| 4,150,436 | 4/1979 | Pemberton | 73/23.1 |

Primary Examiner—Saxfield Chatmon, Jr.
Attorney, Agent, or Firm—C. A. Huggett; William J. Scherback

[57] ABSTRACT

A chromatograph signal generator employs a plurality of Gaussian-waveform generators and a ramp voltage generator. A summing amplifier combines the outputs of such generators to produce a composite chromatographic output.

9 Claims, 2 Drawing Figures

CHROMATOGRAPH SIGNAL GENERATOR

BACKGROUND OF THE INVENTION

In chromatography the output from a chromatograph is called a chromatogram. Generally, a chromatogram is a hard-copy plot of detector output voltage versus time. Ideally, the voltage would appear as a Gaussian-shaped peak, or series of such peaks. For qualitative analytical applications of chromatography, it is essential to know the retention time, i.e., the elapsed time from the start of the chromatogram to the maximum voltage of the peak. For quantitative analysis with a chromatograph it is necessary to know the retention time and the area under the voltage-time peak.

In the current practice of chromatography, the measurement of retention times and peak areas is generally done by electronic integrators. Such chromatographs usually provide hard-copy records of peak areas and retention times in suitable units.

Under ordinary conditions the chromatographer has no method available, other than standard sample injection, to calibrate the output of the integrators. Even with standard sample injection, it must be assumed that the chromatograph is functioning properly.

It is therefore a specific aspect of the present invention to provide apparatus useful in calibrating the output of such chromatographs.

SUMMARY OF THE INVENTION

The present invention is directed toward chromatology and more particularly to a system for calibrating chromatograph electronic integrators.

In accordance with such invention, there is provided a chromatograph signal generator having a plurality of Gaussian-waveform generators, a ramp generator, and means for summing the outputs of the Gaussian-waveform generators and the ramp generator to produce a chromatograph signal output.

First variable means are provided for adjusting the amplitudes of the outputs of the plurality of Gaussian-waveform generators. Second variable means are provided for adjusting the times at which the amplitude peaks of the outputs of the plurality of Gaussian-waveform generators occur. Third variable means are provided for adjusting the slope of the output of the ramp generator.

In a further aspect, each Gaussian-waveform generator employs clock pulses and a counter for accumulating a count of such clock pulses. A programmable read only memory has a preselected Gaussian-transfer function and responds to a predetermined count output of such counter. A digital-to-analog converter provides an analog signal representing the Gaussian-waveform output of such programmable read only memory. The amplitude of such analog signal is adjusted by a variably controlled operational amplifier.

In another aspect, the ramp generator employs clock pulses and a counter for accumulating a count of such clock pulses. A digital-to-analog converter provides an analog signal corresponding to the count output of such counter. The slope of such analog signal is adjusted by a variably controlled operational amplifier.

DESCRIPTION OF THE PREFERRED EMBODIMENT

Figure 1:
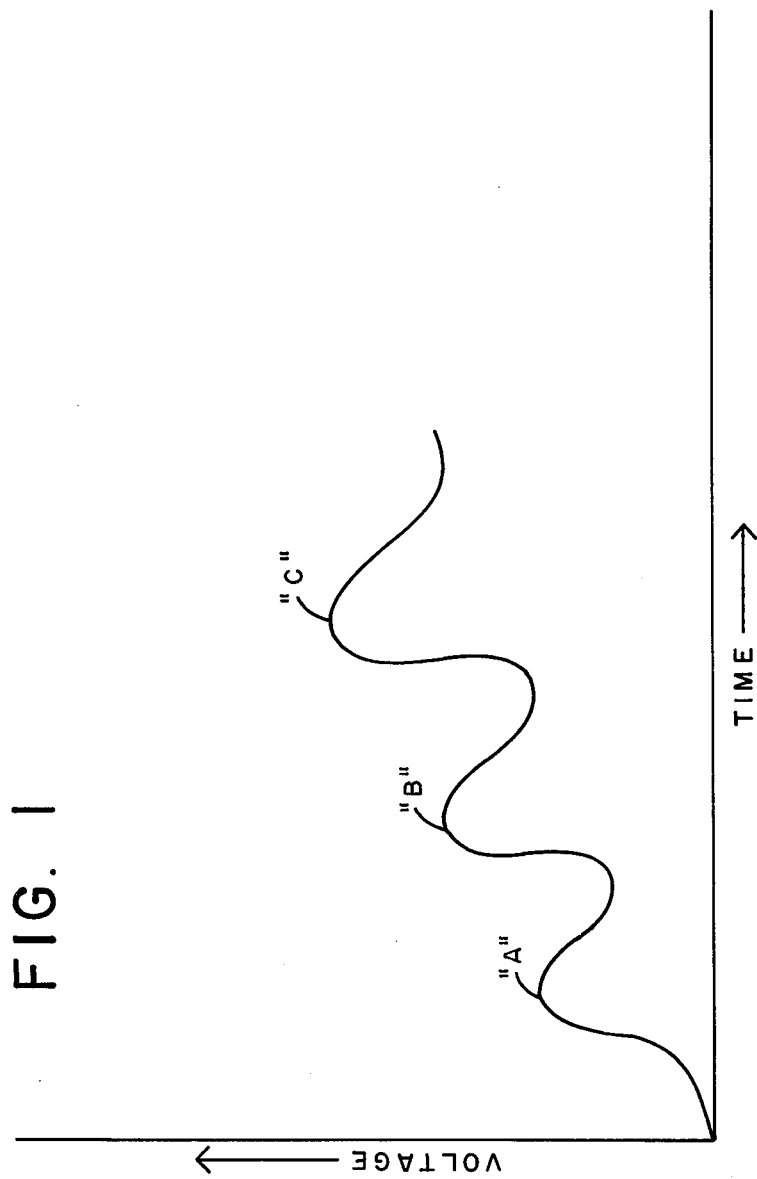
FIG. 1 illustrates a typical Gaussian waveform generated by the chromatograph signal generator of the present invention.

In accordance with the present invention there is provided a chromatograph signal generator which produces an output having Gaussian-shaped voltage amplitude peaks. These amplitude peaks, as well as the time occurrences of such peaks, are variable. FIG. 1 illustrates a typical chromatogram generated by a chromatograph signal generator of the present invention. Accordingly, with a chromatographic output of known characteristics, a conventional chromatograph integrator may be calibrated.

Figure 2:
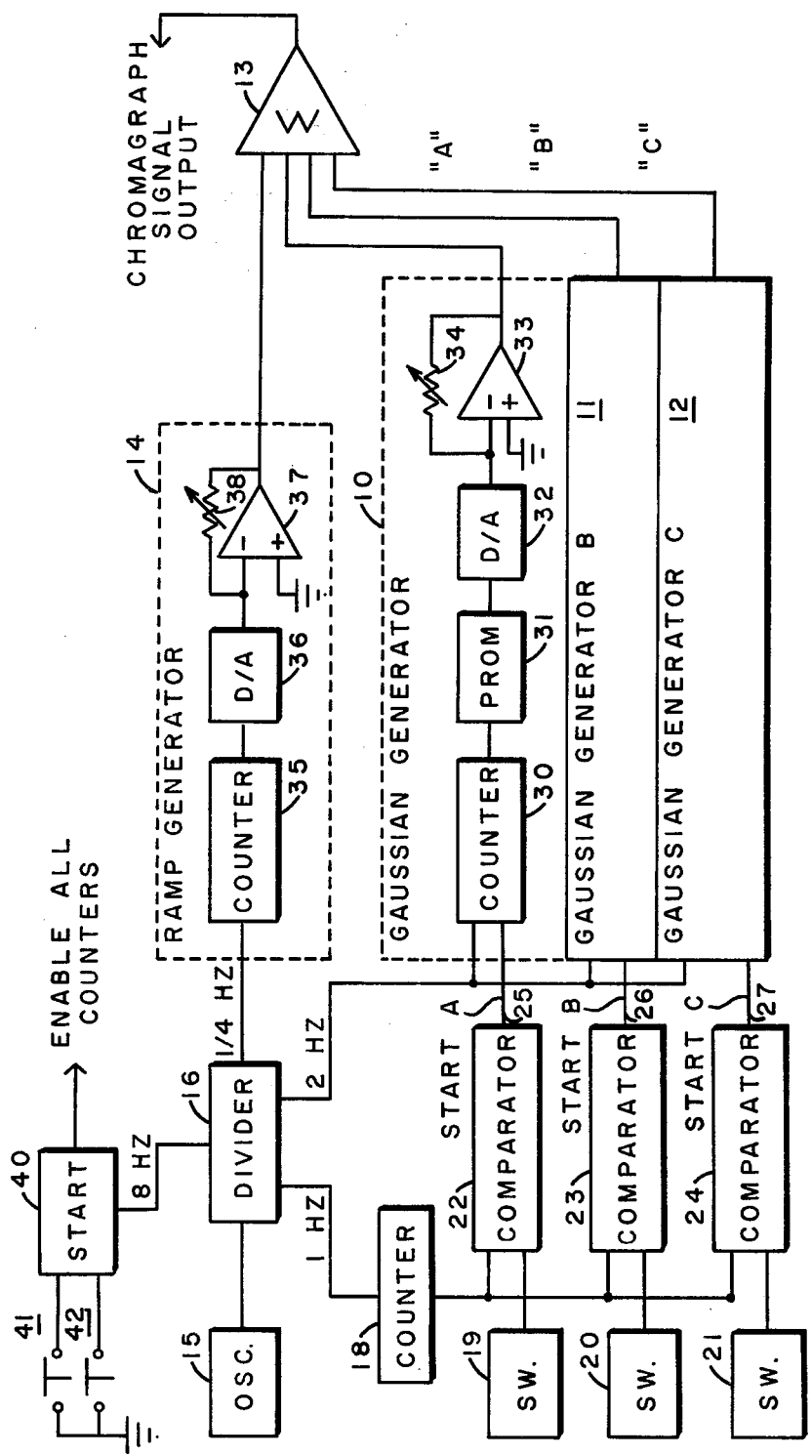
FIG. 2 is an electrical schematic of the chromatograph signal generator of the present invention.

Referring now to FIG. 2 there is illustrated a preferred embodiment of a chromatograph signal generator useful in the calibration of a gas chromatograph integrator. Briefly, three Gaussian generators, 10-12, provide independently controllable Gaussian-waveform signals to a summing amplifier 13. Each signal is variable from zero to one volt, for example. A ramp generator 14 provides a positive-slope ramp signal, such signal being adjustable from zero to one millivolt per second, for example. These four signals, from the three Gaussian generators 10-12 and the ramp generator 14, are added together in the summing amplifier 13 to provide for the desired chromatographic output signal as illustrated in FIG. 1.

Time base for the foregoing-described operation is provided by the crystal oscillator 15 whose 800-KHZ output is divided through frequency divider 16 into four clock frequencies, 8 HZ, 2 HZ, 1 HZ, and ¼ HZ.

The 8-HZ clock is applied to the start flip-flop 40 for enabling all the counters in a synchronous operation. Start and reset of the entire system are provided by the grounded push-button switches 41 and 42 which are connected as inputs to the flip-flop 40. The 1-HZ clock serves as the clock for the seconds counter 18. When the binary value of the seconds counter 18 equals the digital value set on each of the thumbwheel switches 19-21, the digital comparators 22-24 each sends a start signal on lines 25-27, respectively, to the three Gaussian generators 10-12 to start generation of the three Gaussian-waveform signals A, B, and C. The settings of the switches 19-21 determine when the peaks of the Gaussian-waveforms A-C occur, respectively, and not when the start of the waveforms occur. To determine the start of each waveform, the time from the start to the peak is subtracted by presetting the counter to the appropriate number of seconds.

Referring to Gaussian generator 10 only for purposes of illustration, the start signal A on line 25 is applied to the binary counter 30 which is stepped by the 2-HZ clock. The output of counter 30 addresses a Gaussian-transfer function programmable read only memory 31. In such preferred embodiment, a 9-bit signal from the counter 30 addresses the programmable read only memory 31 in 512 time increments. Since the counter is clocked at a 2-HZ rate, it will take 512÷2 or 256 seconds to complete Gaussian-waveform signal A. Eight output bits from memory 31 yield 256 quantized amplitude values for the signal A. This 8-bit output from the memory 31 is converted into an analog voltage by the D/A converter 32. This analog voltage is then coupled to the variably biased operational amplifier 33. Variable resistor 34 controls the amplitude of the Gaussian-waveform signal A from amplifier 33.

The $\theta$-HZ clock is applied to the binary counter 35 of the ramp generator 14. An 8-bit output from the counter 35 is converted into an analog ramp voltage by the D/A converter 36. This ramp voltage is then coupled to the variably biased operational amplifier 37. Variable resistor 38 controls the slope of the ramp voltage.

All three Gaussian-waveform signals A-C from the Gaussian generators 10–12 and the ramp signal from the ramp generator 14 are applied to the summing amplifier 13. This amplifier combines the Gaussian-waveform signals A-C and the ramp signal to provide the desired chromatographic output of the form illustrated in FIG. 1.

It is to be understood that FIG. 2 is merely representative of one embodiment of the present invention. In such embodiment, various types and values of circuit components may be utilized. In accordance with the embodiment of FIG. 2, the following table sets forth specific types of circit components.

TABLE

| Reference Designation | Description |
| --- | --- |
| Oscillator 15 | MK5009P (Mostek) |
| Frequency Divider 16 | SN74161 (Texas Instruments) |
| Flip-flop 40 | SN7473 (Texas Instruments) |
| All counters | SN74160-61 (Texas Instruments) |
| All comparators | SN7485 (Texas Instruments) |
| All operational amplifiers | SN741P (Texas Instruments) |
| All D/A converters | DAC-1C8BC (Datel) |
| All PROMs | HM-7641 (Harris) |
| Variable resistor 34 | 500 ohms |
| Variable resistor 38 | 5 Kohms |

I claim:
1. A chromatograph signal generator comprising:
   (a) a plurality of Gaussian-waveform generators,
   (b) a ramp generator, and
   (c) means for summing the outputs of said plurality of Gaussian-waveform generators and said ramp generator to produce a chromatograph signal output.

2. The generator of claim 1 further including means for adjusting the amplitudes of the outputs of each of said plurality of Gaussian-waveform generators.

3. The generator of claim 1 further including means for adjusting the slope of the output of said ramp generator.

4. The generator of claim 1 further including means for selecting the times at which the amplitude peaks of the outputs of each of said Gaussian-waveform generators occur.

5. The generator of claim 4 wherein said means for selecting the times of said amplitude peaks comprises:
   (a) means for providing clock pulses,
   (b) variable means settable to a predetermined number for each of said plurality of Gaussian-waveform generators, and
   (c) a comparator for each of said plurality of Gaussian-waveform generators, each comparator producing a signal for enabling the corresponding Gaussian-waveform generator when the number of clock pulses produced coincides with the predetermined number set for said corresponding Gaussian-waveform generator.

6. The generator of claim 1 wherein each of said Gaussian-waveform generators comprises:
   (a) means for providing clock pulses,
   (b) a counter for accumulating a count of said clock pulses,
   (c) a programmable read only memory having a selected Gaussian-transfer function responsive to a predetermined count output of said counter, and
   (d) a digital-to-analog converter coupled to the output of said memory for providing an analog Gaussian-waveform output.

7. The generator of claim 6 further including an operational amplifier coupled to the output of said digital-to-analog converter and having variable means for adjusting the amplitude of the Gaussian-waveform output.

8. The ramp generator of claim 1 comprising:
   (a) means for providing clock pulses,
   (b) a counter for accumulating a count of said clock pulses, and
   (c) a digital-to-analog converter coupled to the output of said counter for providing an analog ramp voltage corresponding to the count output of said counter.

9. The ramp generator of claim 8 further including an operational amplifier coupled to the output of said digital-to-analog converter having variable means for adjusting the slope of said ramp voltage.

* * * * *